US005578566A

United States Patent [19]

Bottaro et al.

[11] Patent Number: 5,578,566

[45] Date of Patent: Nov. 26, 1996

[54] KGF RECEPTOR-DERIVED ANTAGONISTS OF KGF BINDING

[75] Inventors: Donald P. Bottaro, Kensington; Jeffrey S. Rubin, Rockville, both of Md.; Stuart A. Aaronson, Great Falls, Va.

[73] Assignee: The United States of America as represented by the Department of Health and Human Services, Washington, D.C.

[21] Appl. No.: 59,030

[22] Filed: May 4, 1993

[51] Int. Cl.[6] .............................. A61K 38/00; C07K 5/00; C07K 7/00

[52] U.S. Cl. ................................ 514/12; 514/13; 514/14; 514/15; 530/324; 530/325; 530/326; 530/327; 530/328

[58] Field of Search .................................... 530/324–327, 530/328; 514/12–14, 15

[56] References Cited

U.S. PATENT DOCUMENTS 3,941,763 3/1976 Sarantakis ................................ 530/313

OTHER PUBLICATIONS

Ron et al., *J. Biol. Chem.*, vol. 268 No. 4, 1993 pp. 2984–2988.

Finch, P. W., et al., "Human KGF Is FGF–Related with Properties of a Paracrine Effector of Epithelial Cell Growth", *Science*, 245:752–755 (18 Aug. 1989).

Miki, T., et al., "Expression cDNA Cloning of the KGF Receptor by Creation of a Transforming Autocrine Loop," *Science*, 251:72–75 (4 Jan. 1991).

Bottaro, D. P., et al., "Characterization of the Receptor for Keratinocyte Growth Factor," *J. Biol. Chem.*, 265(22):12767–12770 (6 Aug. 1990).

Rubin, J. S, "KGF is a Paracrine Mediator of Epithelial Cell Growth," *Proc. Amer. Assoc. Cancer Res.*, 34:588 (Mar. 1993).

Miki, T., et al., "Determination of ligand–binding specificity by alternative splicing: Two distinct growth factor receptors encoded by a single gene," *Proc. Natl. Acad. Sci. USA*, 89:246–250 (Jan. 1992).

*Primary Examiner*—Avis M. Davenport
*Attorney, Agent, or Firm*—Townsend & Townsend & Crew LLP

[57] ABSTRACT

The invention provides KGFR peptides which inhibit binding between keratinocyte growth factor (KGF) and its receptor. The sequence of the peptides is derived from regions in the receptor which specifically bind the growth factor. Also provided are pharmaceutical compositions and methods of inhibiting the interaction of KGF and the receptor in a patient to treat various carcinomas.

16 Claims, 4 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens ( i x ) FEATURE:
( A ) NAME/KEY: Peptide
( B ) LOCATION: 1..20
( D ) OTHER INFORMATION: /label=peptide
/ note="Sequence corresponds to residues 199-218 of the KGF receptor."

( x i ) SEQUENCE DESCRIPTION: SEQ ID NO:1:

```
His Ser Gly Ile Asn Ser Ser Asn Ala Glu Val Leu Ala Leu Phe Asn
1               5                   10                  15

Val Thr Glu Met
            20
```

( 2 ) INFORMATION FOR SEQ ID NO:2:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
( A ) ORGANISM: Homo sapiens ( i x ) FEATURE:
( A ) NAME/KEY: Peptide
( B ) LOCATION: 1..25
( D ) OTHER INFORMATION: /label=peptide
/ note="Sequence corresponds to residues 199-223 of the KGF receptor."

( x i ) SEQUENCE DESCRIPTION: SEQ ID NO:2:

```
His Ser Gly Ile Asn Ser Ser Asn Ala Glu Val Leu Ala Leu Phe Asn
1               5                   10                  15

Val Thr Glu Met Asp Ala Gly Glu Tyr
            20                  25
```

KGF RECEPTOR-DERIVED ANTAGONISTS OF KGF BINDING

BACKGROUND OF THE INVENTION

Growth factors are important mediators of intercellular communication. These molecules are generally released by one cell type and influence proliferation of other cell types. Interest in growth factors has been heightened by evidence of their involvement in neoplasia. For instance, the v-sis transforming gene of simian sarcoma virus encodes a protein that is homologous to the β chain of platelet-derived growth factor. In addition, a number of oncogenes are homologues of genes encoding growth factor receptors. Thus, increased understanding of growth factors and their receptor-mediated signal transduction pathways provides insights into mechanisms of both normal and malignant cell growth.

The fibroblast growth factor (FGF) family affects growth of a wide variety of cells including connective tissue cells and includes acidic fibroblast growth factor (aFGF), basic fibroblast growth factor (bFBF), and the related products of the hst and int-2 oncogenes. Keratinocyte growth factor (KGF) is also a member of this family but is unique in that its activity is restricted to cells of epithelial origin. Biochemical characterization of the KGF receptor (KGFR) suggests that it possesses a high affinity site for KGF and aFGF binding, to which bFGF also binds with much lower affinity. Bottaro et al., *J. Biol. Chem.* 265, 12767–70 (1990). Isolation of the KGFR cDNA has revealed that it is structurally identical to FGF receptor-2 (FGFR-2), except for a stretch of 49 amino acids. In contrast to the KGFR, FGFR-2 binds aFGF and bFGF with high affinity, but exhibits no detectable binding of KGF.

The prior art, however, fails to identify particular regions in KGFR which bind KGF. Without this knowledge, identification of highly specific antagonists of this interaction is difficult. It is widely recognized that the vast majority of human malignancies are derived from epithelial tissues. Thus, identification of compounds which modulate the effect of KGF is important in the treatment of carcinomas as well as other conditions in which ligand-dependent proliferation, mediated by KGFR, contributes to the pathological disorder. The present invention addresses these and other needs.

SUMMARY OF THE INVENTION

The present invention provides compositions comprising KGFR peptides. The peptides of the invention inhibit binding between keratinocyte growth factor and a keratinocyte growth factor receptor and are useful in treating carcinomas and other conditions involving epithelial proliferation.

The peptides of the invention typically consist of between about 15 and about 30 residues. Preferred peptides are those having a sequence substantially identical to a subsequence of the sequence from position 199 to position 247 of keratinocyte growth factor receptor. In particular, a sequence from position 199 to position 218 or from position 199 to position 223. Preferred embodiments are peptide 367 (SEQ ID NO 1) and peptide 412 (SEQ ID. No. 2).

The present invention also provides pharmaceutical compositions comprising a pharmaceutically acceptable excipient and the KGFR peptides of the invention. In certain embodiments the peptides may comprise modifications to improve pharmacological properties. Such modifications include the use of one or more D-amino acid or an amino acid mimetic in the peptides.

The invention further provides methods of inhibiting binding between a keratinocyte growth factor and a keratinocyte growth factor receptor in a patient. The methods comprise administering to the patient a therapeutically effective dose of a pharmaceutical composition comprising pharmaceutically acceptable excipient and the KGFR peptides. The methods of the invention can be used to treat conditions associated with KGF-mediated proliferation such as carcinomas.

Also disclosed are methods of assaying test compounds for the ability to inhibit KGFR-mediated cell proliferation. The methods comprise contacting a test compound with an KGFR peptide and a keratinocyte growth factor and detecting the ability of the test compound to inhibit binding between the KGFR peptide and the keratinocyte growth factor. The test compound can be a biomolecule such as a polypeptide or an immunoglobulin. The KGFR peptides used in the methods are preferably peptide 367 (SEQ ID. No. 1) or peptide 412 (SEQ ID. No. 2). In a preferred assay format the KGFR peptide is labelled and the keratinocyte growth factor is immobilized on a solid surface.

DEFINITIONS

As used herein, a "peptide" "polypeptide" or "oligopeptide" is series of residues, typically L-amino acids, connected one to the other typically by peptide bonds between the alpha-amino and carbonyl groups of adjacent amino acids.

A "KGFR peptide" is one having a sequence derived from a portion of KGFR that specifically binds KGF and thus inhibits the mitogenic activity of KGF. A KGFR peptide can comprise a sequence from KGFR (e.g., residues 199–223 or 199–218) or one substantially identical to it. The term also encompasses various analogs of such sequences, as described below.

The phrases "isolated" or "biologically pure" refer to material which is substantially or essentially free from components which normally accompany it as found in its native state. Thus, the KGFR peptides of this invention do not contain materials normally associated with their in situ environment, e.g., other proteins from a keratinocyte cell membrane. Even where a protein has been isolated to a homogenous or dominant band by PAGE, there can be trace contaminants in the range of 5–10% of native protein which co-purify with the desired protein. Isolated peptides of this invention do not contain such endogenous co-purified protein.

The term "residue" refers to an amino acid (D or L) or amino acid mimetic incorporated in a oligopeptide by an amide bond or amide bond mimetic. An amide bond mimetic of the invention includes peptide backbone modifications well known to those skilled in the art.

DESCRIPTION OF THE PREFERRED EMBODIMENT

Figure 1:
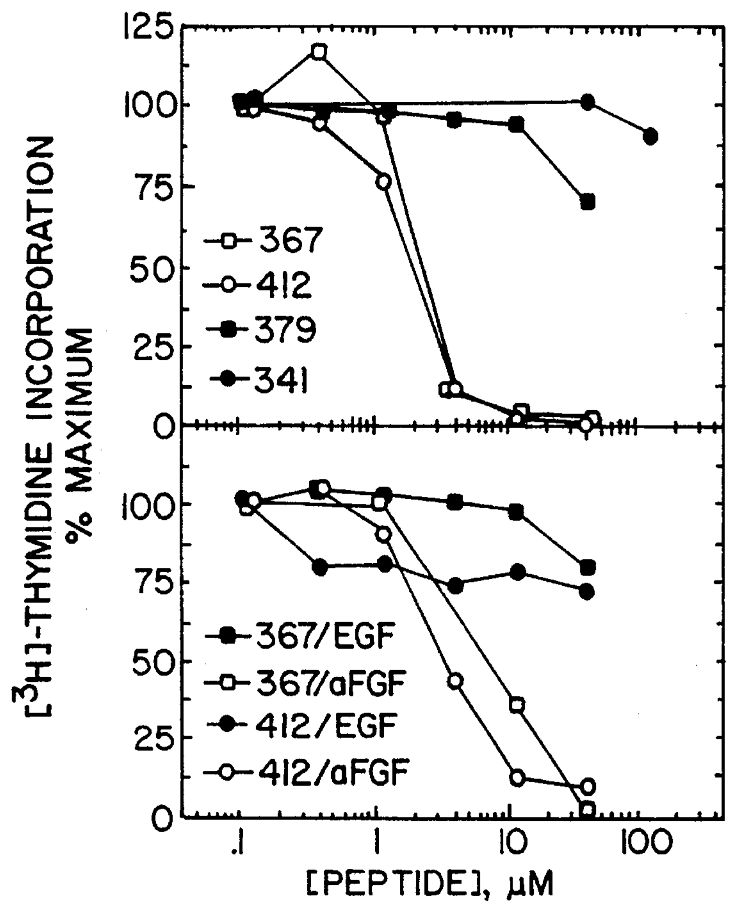
FIG. 1 shows inhibition of growth factor-induced DNA synthesis in Balb/MK cells as a function of peptide concentration. Upper Panel: Effects of peptides 367 (SEQ ID NO 1), 412 (SEQ ID NO 2), 379, and 341 on KGF-induced DNA synthesis. Lower Panel: Effects of peptides 367 (SEQ ID NO 1) and 412 (SEQ ID NO 2) on aFGF- and EGF-induced DNA synthesis. Values are expressed as a percentage of the value observed for cells treated with a half-maximal dose of growth factor (1 ng/ml for KGF; 3 ng/ml for aFGF and EGF). The mean raw value for unstimulated control cells was 300 cpm/well; the mean raw values for KGF, AFGF, and EGF stimulated cells were approximately 65,000, 25,000 and 35,000 cpm/well, respectively. Values shown are the mean of triplicate samples. Standard deviations were typically less than ±7%. Results are representative of three separate experiments.

The present invention provides KGFR peptides which inhibit binding between KGF and KGFR. KGF was originally purified from conditioned medium of human embryonic lung fibroblasts and is mitogenic for a variety of epithelial cell types, such as bronchial epithelial cells, Type 2 pneumocytes, prostatic epithelial cells, hepatocytes, mammary epithelial cells, and keratinocytes. (Aaronson et al., *Ann. New York Acad. Sci.* 638:62–77 (1991), which is incorporated herein by reference). Its receptor, KGFR, is a membrane spanning tyrosine kinase which also binds aFGF with high affinity (Bottaro et al., *J. Biol. Chem.* 265, 12767–70 (1990), which is incorporated herein by reference). KGF differs from other members of the FGF family, which are active on a broad range of cell types, in that its activity is restricted to epithelial cells. Thus, inhibition of the interaction between KGF and KGFR is particularly useful in the treatment of carcinomas and other conditions involving epithelial proliferation.

KGFR is encoded by the bek/FGFR2 gene, whose alternative transcript specifies a FGF receptor (FGFR-2) with high affinity for aFGF and bFGF, but no detectable binding of KGF. Both receptors are membrane spanning tyrosine kinases which contain three Ig loops in the extracellular domain and an acidic amino acid stretch between the first and second loops. These two receptors differ structurally in a 49 amino acid segment (residues 199–147) spanning the carboxyl half of the third Ig loop and extending into the stem region. PCR analysis of genomic DNA demonstrated that this region of divergence between the KGFR and FGFR-2 is determined by alternative exons, referred to as the K and B exons. Miki et al., *Proc. Natl. Acad. Sci. U.S.A.* 89:246–50 (1992), which is incorporated herein by reference.

The present invention is based in part on the discovery of peptides corresponding to regions within the 49 amino acid segment which specifically bind KGF and thus block interactions between KGF and its receptor. In addition, it has been found that one such peptide antagonist and a monoclonal antibody against KGF that neutralizes mitogenic activity compete for binding to the same site on the growth factor. Thus the region of the receptor represented by this peptide binds directly to KGF. It has also been found that heparin, which also blocks KGF mitogenic activity, and the monoclonal KGF antibody, recognize distinct sites on the KGF molecule. Both of these sites on KGF appear to overlap the peptide-defined receptor binding site.

KGFR peptides can be made using any of a number of standard techniques. Conveniently, they can be synthesized by conventional techniques employing automatic synthesizers, such as the Beckman, Applied Biosystems, or other commonly available peptide synthesizers using well known protocols. They can also be synthesized manually using techniques well known in the art. See, e.g. Stewart and Young, *Solid Phase Peptide Synthesis,* (Rockford, Ill., Pierce), 2d Ed. (1984), which is incorporated herein by reference.

Alternatively, DNA sequences which encode a protein (e.g., a portion of KGFR) comprising the particular peptide may be cloned and expressed to provide the peptide. Cells which express KGFR can be used as a source of the DNA sequences. Appropriate cells include those of epithelial origin such as human B5/589 (mammary epithelial cells) bronchial epithelial cells, Type 2 pneumocytes, prostatic epithelial cells, hepatocytes, and keratinocytes. Standard techniques can be used to screen cDNA libraries to identify sequences encoding the desired sequences (see, Sambrook et al., *Molecular Cloning—A Laboratory Manual,* Cold Spring Harbor Laboratory, Cold Spring Harbor, N.Y., 1989, which is incorporated herein by reference). For example, Miki et al. (1992), supra, describe cloning KGFR cDNA from B5/589 cells.

KGFR can also be conveniently isolated from the cell types noted above using standard protein purification techniques. The protein can be purified by any of a variety of known techniques, including, for example, reverse phase high-performance liquid chromatography (HPLC), ion-exchange or immunoaffinity chromatography, separation by size, or electrophoresis (See, generally, Scopes, R., *Protein Purification,* Springer-Verlag, N.Y. (1982), which is incorporated herein by reference). Isolation of KGFR from keratinocytes is described in Bottaro et al., supra.

Typically, the KGFR peptides of the invention will comprise amino acid sequences corresponding, or substantially identical, to amino acid sequences encoded by the K exon of the BEK gene. Two oligopeptides are said to be "identical" if the sequence of amino acid residues in the two sequences is the same when aligned for maximum correspondence.

Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package, Genetics Computer Group (GCG), 575 Science Dr., Madison, Wis.), or by inspection. These references are incorporated herein by reference.

"Percentage of sequence identity" is determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 60% sequence identity, preferably at least 80%, more preferably at least 90% and most preferably at least 95%, compared to a reference sequence using the programs described above using standard parameters.

The KGFR peptides of the invention typically comprise at least about 10 residues, preferably at least about 15 residues, more preferably about 20. Preferably, they will not exceed about 50 residues, preferably less than about 30, more preferably about 20 residues.

The KGFR peptides of the invention may comprise modifications of the sequences from KGFR. The modifications can be selected, for example, to affect the interaction with KGF, or to alter their in vivo stability. For instance, inclusion of one or more D-amino acids in the peptide typically increases stability, particularly if the D-amino acid residues are substituted at one or both. termini of the peptide sequence. Stability can be assayed in a variety of ways such as by measuring the half-life of the proteins during incubation with peptidases or human plasma or serum. A number of such protein stability assays have been described (see, e.g., Verhoef et al., *Eur. J. Drug Metab. Pharmacokin.* 11:291–302 (1986), which is incorporated herein by reference).

The peptides can also be modified by linkage to other molecules. For example, different N- or C-terminal groups may be introduced to alter the molecule's physical and/or chemical properties. Such alterations may be utilized to affect, for example, adhesion, stability, bio-availability, localization or detection of the molecules. For diagnostic purposes, a wide variety of labels may be linked to the terminus, which may provide, directly or indirectly, a detectable signal. Thus, the peptides of the subject invention may be modified in a variety of ways for a variety of end purposes while still retaining biological activity.

Various reactive sites may be introduced at the terminus for linking to particles, solid substrates, macromolecules, or the like. For example, an internal amino moiety of a growing chain bound to a solid substrate with the intermediate side groups protected, may be conjugated with methyldithiobenzoic acid (MDTB). The free mercaptan group may then be used for conjugating with activated olefins. Thus, proteins, such as serum albumin, keyhole limpet hemocyanin, bovine B-globulin, or the like, may be conjugated to the peptide to provide for an immunogen to produce antibodies to the peptide for use in immunoassays, for affinity chromatography, or the like. Alternatively, the peptide can be bonded to another polypeptide by preparing a DNA sequence which has the peptide at the N-terminus, C-terminus or internal to the protein, so as to provide a fused protein which includes the KGF peptide of interest.

Thus, in addition to peptides derived directly from KGFR amino acid sequences, a number of conformational analogs of those sequences can be used. The ability of analogs to bind KGF and inhibit its activity can be tested in the assays described below. As used herein, "conformational analogs" are molecules having spatial or polar organization sufficiently similar to the amino acid sequences of the KGF binding region of KGFR to inhibit binding. The conformational analogs of the invention may consist entirely of amino acid residues other than those found in the KGFR sequence.

Alternatively, they may comprise any of a number of amino acid mimetics linked by peptide bond mimetics. Such modifications include modifications of the amide nitrogen, the α-carbon, amide carbonyl, complete replacement of the amide bond, extensions, deletions or backbone crosslinks. See, generally, Spatola, *Chemistry and Biochemistry of Amino Acids, Peptides and Proteins,* Vol. VII (Weinstein ed., 1983), which is incorporated herein by reference. Several peptide backbone modifications are known, these include, $\psi[CH_2S]$, $\psi[CH_2NH]$, $\psi[CSNH_2]$, $\psi[NHCO]$, $\psi[COCH_2]$ and $\psi[(E)$ or $(Z)$ $CH{=}CH]$. The nomenclature used above, follows that suggested by Spatola, supra. In this context, ψ indicates the absence of an amide bond. The structure that replaces the amide group is specified within the brackets.

An "amino acid mimetic" as used here is a moiety other than a naturally occurring amino acid that conformationally and functionally serves as a substitute for an amino acid in a peptide of the present invention. Such a moiety serves as a substitute for an amino acid residue if it does not substantially interfere with the ability of the peptide to bind to KGF. Amino acid mimetics may include non-protein amino acids, such as β-γ-δ-amino acids, β-γ-δ-imino acids (such as piperidine-4-carboxylic acid) as well as many derivatives of L-α-amino acids. A number of suitable amino acid mimetics are known to the skilled artisan, they include cyclohexylalanine, 3-cyclohexylpropionic acid, L-adamantyl alanine, adamantylacetic acid and the like. Peptide mimetics suitable for peptides of the present invention are discussed by Morgan and Gainor, *Ann. Repts. Med. Chem.* 24:243–252 (1989), which is incorporated herein by reference.

The KGFR peptides of the invention can also be used to raise blocking polyclonal or monoclonal antibodies, which are specific for the region of KGFR which binds KGF. The multitude of techniques available to those skilled in the art for production and manipulation of various immunoglobulin molecules can thus be readily applied to inhibit binding. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and $F(ab)_2$, as well as in single chains. For a general review of immunoglobulin structure and function see, *Fundamental Immunology,* 2d Ed., W. E. Paul ed., Ravens Press, N.Y., (1989).

Antibodies which bind KGFR peptides domain may be produced by a variety of means. The production of non-human monoclonal antibodies, e.g., murine, lagomorpha, equine, etc., is well known and may be accomplished by, for example, immunizing the animal with a preparation containing the KGFR peptide. Antibody-producing cells obtained from the immunized animals are immortalized and screened, or screened first for the production of antibody which inhibits binding between KGF and KGFR and then immortalized. For a discussion of general procedures of monoclonal antibody production see Harlow and Lane, *Antibodies, A Laboratory Manual* Cold Spring Harbor Publications, N.Y. (1988), which is incorporated herein by reference.

The monoclonal antibodies, peptides comprising amino acid substitutions and other conformational analogs can be assayed for biological activity in a number of different ways. For instance, assays can be used to detect the ability of the compounds to inhibit the action of KGF by measuring proliferation of appropriate cells. Cell proliferation is conveniently measured by [$^3$H]-thymidine incorporation using standard techniques. Alternatively, the ability of the test compound to block binding of labeled KGF to appropriate cells can be measured. Examples of such assays are presented in the Example section below.

The ability of peptides to modulate mitogenic activity of KGF in vitro may also be correlated with their ability to affect the response in vivo, For instance, animal models of particular carcinomas can be used to demonstrate the efficacy of the peptides of the invention. Typically nude mouse xenograft models are used to test the therapeutic utility of agents for the treatment of cancer. Such models are well known to one of skill in the art. For a summary of models commonly used in the art see, Khleif et al., in Cancer Medicine, 3rd edition, Section 15, part 5, Holland et al., eds. (Lea and Febiger, Malvern Pa., 1993), which is incorporated herein by reference.

In addition, because the present invention provides the regions within KGFR which bind KGF peptides of the invention can be used to analyze the structure of the KGF-KGFR complex using, for instance, NMR and x-ray crystallographic techniques. Examination of the crystal structure of the complex provides information on the precise regions on both KGF and KGFR required for binding. For a description of this approach to analyzing receptor-ligand interactions see, de Vos et al., *Science* 255:306–312 (1992). Knowledge obtained by these studies is particularly useful in rational drug design (see, e.g., Fuh et al., *Science* 256:1677–1680 (1992)).

The peptides of the invention are particularly useful in rational drug design in screening test compounds, e.g. modified peptides, for the ability to inhibit binding between KGFR peptides and KGF. Test compounds used in the assays of the present invention can be synthetic or naturally-produced biomolecule, such as a polypeptide, immunoglobulin, carbohydrate (e.g., oligosaccharide), glycoconjugate, nucleic acid, and the like.

A number of assay formats can be used. For example, KGF can be immobilized on a solid surface and the ability of the modified peptide or other test compound to competitively inhibit binding of labelled KGFR peptides can be measured. Alternatively, the KGFR peptides can be immobilized on the surface through the use of appropriate linkers well known to those of skill in the art. Using such formats, large numbers of specific modifications, (e.g., substitutions, deletions or additions) can be screened. Alternatively, the ability of modified peptides or other test compounds to inhibit KGF mediated cell proliferation can be measured using KGFR peptides as controls. Assays such as those described in the Example section, below, can be used for this purpose.

Methods for synthesizing polypeptides of defined composition are well known in the art, as described above. The polypeptides can be altered in a systematic way to identify the sequence of residues which have the desired effect (see, e.g., U.S. Pat. No. 4,833,092, which is incorporated herein by reference).

Many assay formats employ labelled assay components. The labelling systems can be in a variety of forms. The label may be coupled directly or indirectly to the desired component of the assay according to methods well known in the art. A wide variety of labels may be used. The component may be labelled by any one of several methods. The most common method of detection is the use of autoradiography with $^3$H, $^{125}$I, $^{35}$S, $^{14}$C, or $^{32}$P labelled compounds or the like. Non-radioactive labels include ligands which bind to labelled antibodies, fluorophores, chemiluminescent agents, enzymes, and antibodies which can serve as specific binding pair members for a labelled ligand. The choice of label depends on sensitivity required, ease of conjugation with the compound, stability requirements, and available instrumentation.

The peptides are useful in therapeutic applications, particularly in the treatment of carcinomas. Malignancies treatable by peptides of the invention include, but are not limited to, cancers of the prostate, skin, breast, lung and liver. Other conditions include proliferative epithelial disorders such as adenomas, polyps, psoriasis, and the like.

Pharmaceutical compositions of the invention are suitable for use in a variety of drug delivery systems. Suitable formulations for use in the present invention are found in *Remington's Pharmaceutical Sciences,* Mack Publishing Company, Philadelphia, Pa., 17th ed. (1985), which is incorporated herein by reference. For a brief review of methods for drug delivery, see, Langer, *Science* 249:1527–1533 (1990), which is incorporated herein by reference.

The subject peptides, by themselves or as conjugates, may be prepared as formulations in pharmaceutically acceptable media, for example saline, PBS, and glucose, generally at a therapeutically effective dose, the concentrations of which will be determined empirically in accordance with conventional procedures for the particular purpose. The additives may include bactericidal agents, stabilizers, buffers, or the like.

In order to enhance serum half-life, the peptides may be encapsulated, introduced into the lumen of liposomes, prepared as a colloid, or other conventional. technique may be employed which provides an extended serum half-life of the peptides. A variety of methods are available for preparing liposomes, as described in, e.g., Szoka et al., *Ann. Rev. Biophys. Bioeng.* 9:467 (1980), U.S. Pat. Nos. 4,235,871, 4,501,728 and 4,837,028, all of which are incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the severity of the disease and the weight and general state of the patient.

The pharmaceutical compositions are intended for parenteral, topical, oral or local administration, such as by aerosol or transdermally, for prophylactic and/or therapeutic treatment. Commonly, the pharmaceutical compositions are administered parenterally, e.g., intravenously. Thus, the invention provides compositions for parenteral administration which comprise KGFR peptide dissolved or suspended in an acceptable carrier, preferably an aqueous carrier, e.g., water, buffered water, 0.4% saline, 0.3% glycine, hyaluronic acid and the like. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The compositions may contain pharmaceutically acceptable auxiliary substances as required to approximate physiological conditions, such as pH adjusting and buffering agents, tonicity adjusting agents, wetting agents, detergents and the like, for example, sodium acetate, sodium lactate, sodium chloride, potassium chloride, calcium chloride, sorbitan monolaurate, triethanolamine oleate, etc.

The concentration of KGFR peptides in the pharmaceutical formulations can vary widely, i.e., from less than about 0.01%, usually at or at least about 5% to as much as 50 to 75% by weight and will be selected primarily by fluid volumes, viscosities, etc., in accordance with the particular mode of administration selected. Thus, a typical pharmaceutical composition for intravenous infusion could be made up to contain 250 ml of sterile Ringer's solution, and 10 mg of peptide.

For parenteral administration, the therapeutic dosage of the peptides of the present invention will vary according to, for example, the particular use for which the treatment is made, the manner of administration of the peptides, the health and condition of the patient, and the judgment of the prescribing physician. For example, for the treatment of breast cancer with a peptide of the present invention, the dose will typically be in the range of about 1 mg to about 1000 mg per day, preferably about 10 to about 250 per day, for a 70 kg patient.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, preferably 25–75%.

For aerosol administration, the KGFR peptides are preferably supplied in finely divided form along with a conventional non-toxic surfactant and a suitable propellant. Typical percentages of peptides are 0.01%–20% by weight, preferably 1%–10%; and of surfactant from 0.1%–20% by weight, preferably 0.25%–5%.

Two or more peptides of the invention may be combined to form a peptide "cocktail" under certain circumstances for increased efficacy. The peptides of the invention may also be used in conjunction with other pharmaceutically active agents.

The following example is offered by way of illustration and not by limitation.

EXAMPLE 1

This example shows that synthetic peptides corresponding to part of the region encoded by exon K antagonize the interaction between KGF and its receptor. In particular, the results demonstrate that peptide antagonists and a monoclonal antibody against KGF that neutralizes mitogenic activity compete for binding to the same site on the growth factor. The results also show that heparin, which also blocks KGF mitogenic activity, and the monoclonal KGF antibody, recognize distinct sites on the KGF molecule.

I. EXPERIMENTAL PROCEDURES

Materials

Recombinant human KGF was prepared as described in Ron et al., *J. Biol. Chem.* 268:2984–2988 (1993), which is incorporated herein by reference. Acidic and basic FGF purified from bovine brain were obtained from Upstate Biotechnology, Inc. [$^{125}$I]Na(>5000 Ci/mM) was purchased from Amersham. Recombinant KGF was radiolabeled with [$^{125}$I]Na by the chloramine-T method as described previously Bottaro et al., supra. Heparin (sodium salt) purified from bovine lung was obtained from Sigma. Mouse monoclonal antibody against KGF (designated 1G4) was obtained using purified recombinant KGF as antigen. 1G4 completely neutralizes KGF mitogenic activity, as observed by [$^{3}$H]-thymidine incorporation into DNA, at concentrations as low as 10 ng/ml. 1G4 IgG was purified using GammaBind-G Sepharose (Pharmacia). The composition of synthetic peptides (Peninsula. Labs) was confirmed by amino acid analysis; two successive rounds of reversed-phase HPLC yielded >98% purity. Peptides corresponding to residues 199–218 and 199–223 of the KGF receptor sequence (HSGINSSNAEVLALFNVTEM and HSGINSSNAEVLALFNVTEMDAGEY) were designated 367 (SEQ ID NO 1) (SEQ ID NO 1) and 412 (SEQ ID NO 2), respectively. Control peptides included a randomized version of peptide 367 (SEQ ID NO 1) (designated peptide 379), and several peptides of similar length and composition (peptides 341, 275, 323, and 324).

[$^{3}$H]-Thymidine incorporation assays

Incorporation of [$^{3}$H]-thymidine into Balb/MK or NIH/3T3 cells was performed as described in Rubin et al., *Proc. Natl. Acad. Sci. U.S.A.* 86:802–806 (1989), which is incorporated herein by reference. A half-maximal dose of recombinant KGF (1 ng/ml), aFGF, bFGF, or EGF (3 ng/ml each) was added to each well as indicated. Peptides dissolved in 50% acetonitrile in distilled water (5 mg/ml stock solution for peptides of the invention) or in distilled water alone (all other peptides) were added as indicated. Peptide 412 (SEQ ID NO 2) was water soluble at concentrations >3000-fold higher than its highest $ED_{50}$; peptide 367 (SEQ ID NO 1) (SEQ ID NO 1) reached its limit of solubility in water at 125 μM, or approximately 30-fold higher than its highest $ED_{50}$.

Receptor Binding Assays

[$^{125}$I]-KGF binding to NIH/3T3 cells overexpressing KGFR was measured as described in Bottaro et al., supra. Competition studies were performed with unlabeled KGF or peptides as indicated.

KGF Radioimmunoassay

[$^{125}$I]-KGF was immunoprecipitated by 1G4 in the presence of unlabeled KGF, aFGF, or peptides as indicated. Briefly, 1G4 (4 ng/ml final concentration), [$^{125}$I]-KGF (30,000 cpm), and appropriate competitors were mixed in 200 μl of buffer containing 10 mM Tris (pH 7.4), 130 mm NaCl, 1 mM EDTA, 10 mM KC1, 1% NP-40, 0.1% SDS, 0.05% Tween-20, and 0.3% nonfat dry milk, and incubated for 24h at 4° C. Antigen-antibody complex was recovered by adding 30 ul (50% suspension) GammaBind-G Sepharose, incubating an additional 30 min at 4° C. (turning gently), and brief centrifugation (5 min at 14,000×g, 4° C.). Pelleted material was washed three times (0–5 ml each) with cold buffer, and radioactivity was measured by gamma counting.

II. RESULTS

As shown in FIG. 1, incubation of Balb/MK cells with peptides 367 (SEQ ID NO 1, corresponding to KGFR residues 199–218) or 412 (SEQ ID NO 2, corresponding to residues 199–223) was associated with dose-dependent inhibition of KGF-stimulated DNA synthesis, with 50% inhibition at ~1.6 μM. A control peptide having identical amino acid composition but random sequence (peptide 379), and a second control peptide with similar composition (peptide 341) had no significant effect.

It has been reported previously that aFGF binds to the KGFR with high affinity, and effectively competes for KGF binding to Balb/MK cells (Bottaro et al., supra). Peptides 367 (SEQ ID NO 1) (SEQ ID NO 1) and 412 (SEQ ID NO 2) also inhibited aFGF-induced DNA synthesis in Balb/MK (50% inhibition at ~3 μM; FIG. 1). Neither peptide significantly inhibited the mitogenic activities of bFGF (data not shown) or EGF under the same conditions (FIG. 1), indicating that their effects were growth factor specific.

Figure 2:
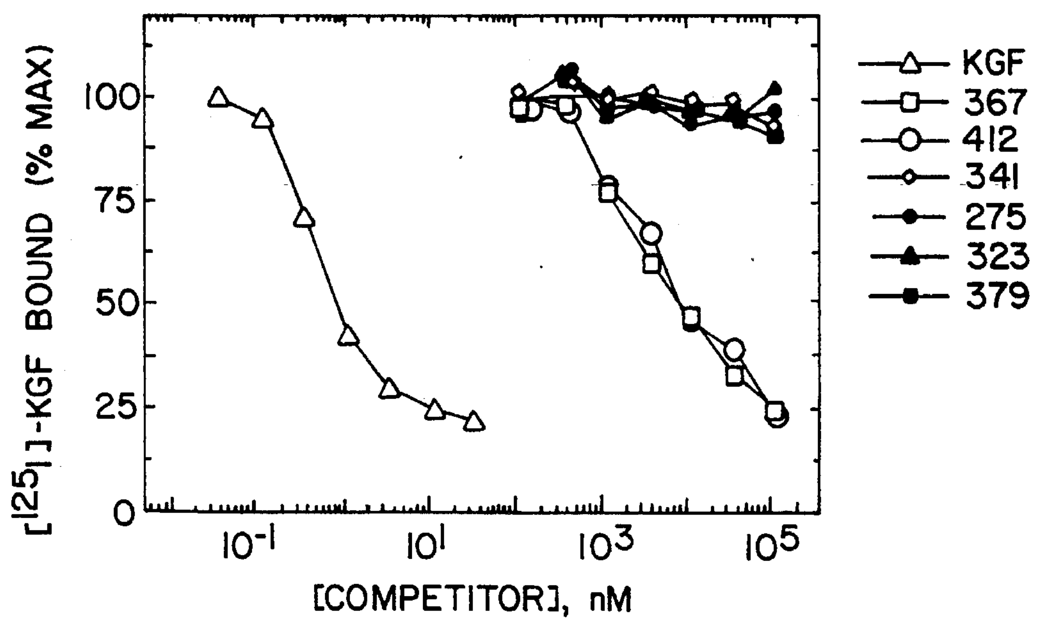
FIG. 2 shows specific binding of [$^{125}$I]-KGF to NIH/3T3 cells overexpressing the KGF receptor, competed by increasing concentrations of KGF, or peptides 367 (SEQ ID NO 1), 412 (SEQ ID NO 2), 341, 275, 323, or 324. Values shown are the mean of triplicate samples. Results are representative of three separate experiments.

To characterize the mechanism of inhibition, peptides 367 (SEQ ID NO 1) and 412 (SEQ ID NO 2) were compared to KGF for their ability to compete directly for [$^{125}$I]-KGF binding on NIH3T3/KGFR transfectants (FIG. 2). Of 6 synthetic peptides with similar amino acid composition and size (including peptide 379), only peptides 367 (SEQ ID NO 1) and 412 (SEQ ID NO 2) competed specifically for [$^{125}$I]-KGF binding. Displacement of 50% of the radiolabeled KGF was achieved at ~4 μM for both peptides. This was a 10,000-fold excess relative to the concentration of unlabeled KGF required, or relative to the concentration of KGFR present. Both peptides also blocked the binding of radiolabeled aFGF to the same KGFR transfectants (data not shown). These results suggested that peptides 367 (SEQ ID NO 1) and 412 (SEQ ID NO 2) antagonized KGF and aFGF-induced DNA synthesis by preventing their interaction with the KGFR.

To exclude the possibility that inhibition of ligand/receptor binding resulted from an interaction between peptide and receptor that changed receptor conformation, or interfered with normal receptor/receptor interactions, the following experiments were performed. It was reasoned that if these peptides antagonized ligand/receptor interactions by binding to the growth factor, then the effect might be observed regardless of which FGF receptor was used in the assay system. Although KGF appears to act only on cells of epithelial origin, aFGF acts on a variety of cell types including endothelial cells and fibroblasts, and binds to both FGFR-1 and FGFR-2 with high affinity.

Figure 3:
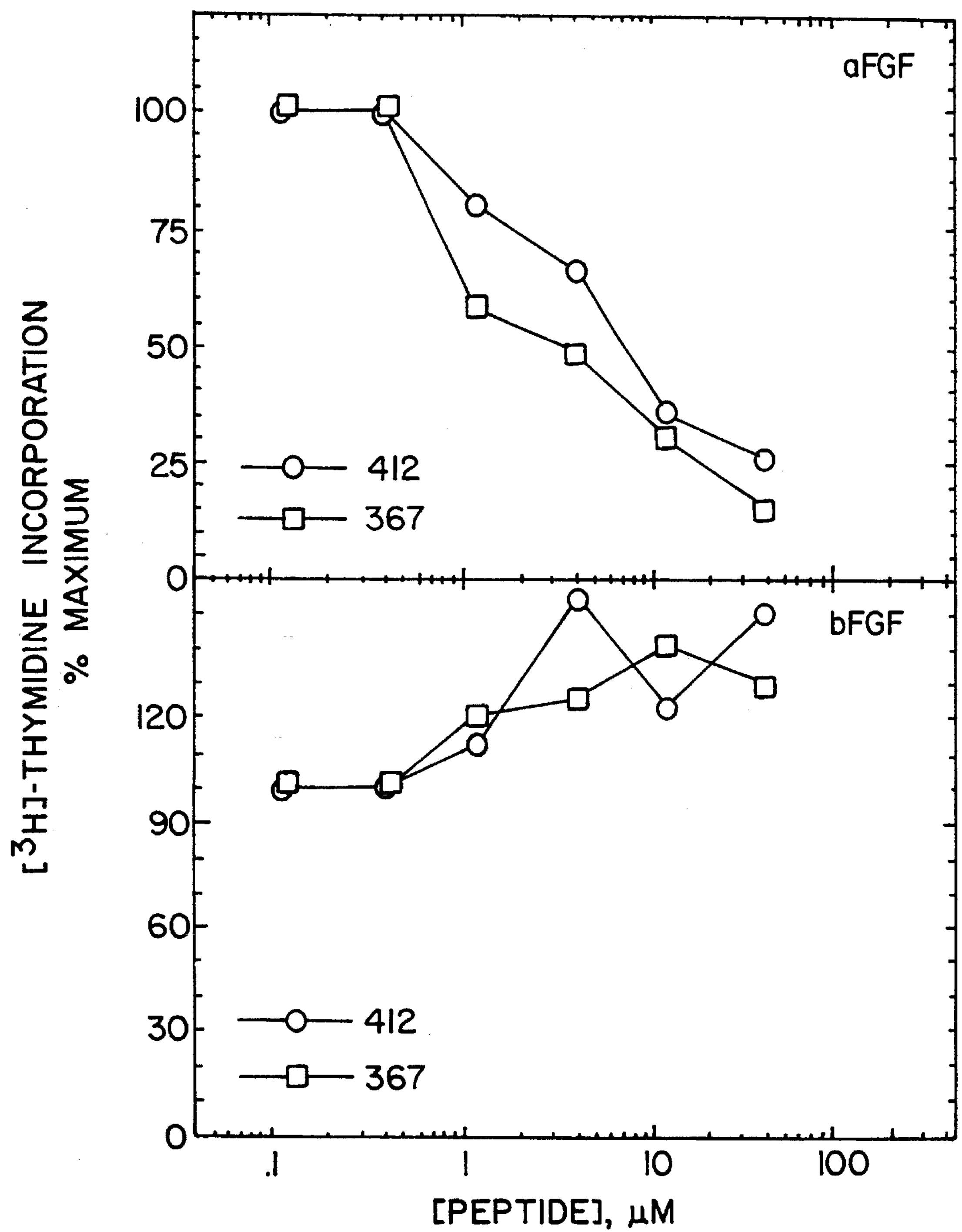
FIG. 3 shows DNA synthesis in NIH/3T3 cells as a function of peptide concentration. Upper Panel: Effects of peptides 367 (SEQ ID NO 1) and 412 (SEQ ID NO 2) on aFGF-induced DNA synthesis. Lower Panel: Effects of peptides 367 (SEQ ID NO 1) and 412 (SEQ ID NO 2) on bFGF-induced DNA synthesis. The mean raw value for untreated cells was 900 cpm/well; the mean raw values for AFGF and BFGF stimulated cells were approximately 20,000 and 25,000 cpm/well, respectively. Values shown are the mean of triplicate samples. Results are representative of three separate experiments.

As shown in FIG. 3, peptides 367 (SEQ ID NO 1) and 412 (SEQ ID NO 2) were as effective at blocking aFGF-induced mitogenesis in NIH/3T3 fibroblasts, which express predominantly FGFR-1, as they were in Balb/MK cells, which express predominantly FGFR-2. In contrast, neither peptide blocked bFGF-induced mitogenesis, which is also mediated by FGFR-1 in NIH/3T3 cells (FIG. 3). These results strongly suggest that peptides 367 (SEQ ID NO 1) and 412 (SEQ ID NO 2) inhibited ligand/receptor interactions by binding directly to KGF or acidic FGF.

Figure 4:
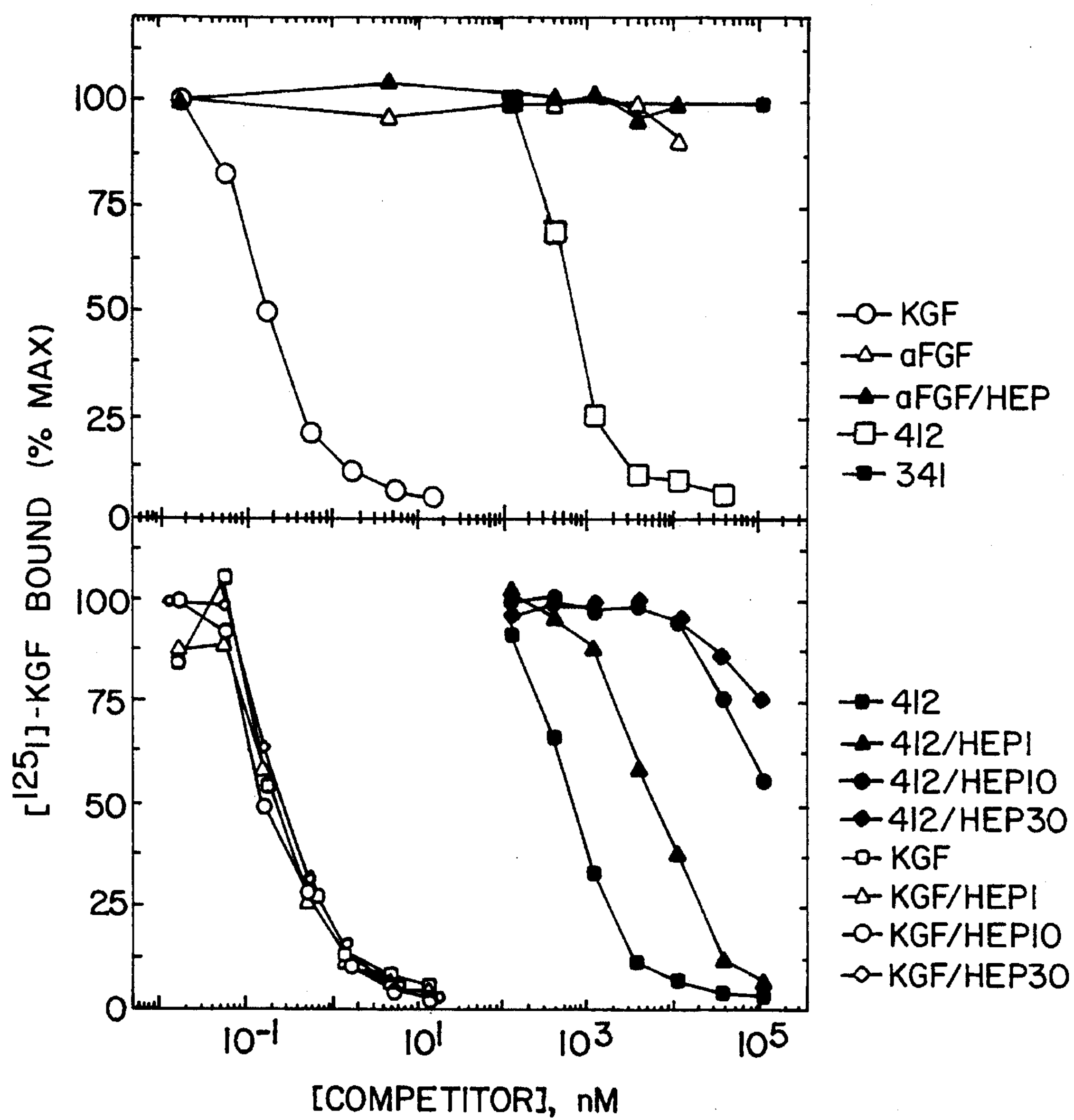
FIG. 4 shows the results of a KGF radioimmunoassay using monoclonal antibody 1G4. Upper Panel: Immunoprecipitation of [$^{125}$I]-KGF competed by KGF, aFGF, aFGF+heparin (30 μg/ml), peptide 412 (SEQ ID NO 2) or peptide 341. Lower Panel: Immunoprecipitation of [$^{125}$I]-KGF competed by KGF, KGF+heparin (1, 10, or 30 μg/ml, as indicated), peptide 412 (SEQ ID NO 2), or peptide 412 (SEQ ID NO 2)+heparin (1, 10, or 30 μg/ml, as indicated). Values are the mean of duplicate samples, expressed as % maximum [$^{125}$I]-KGF bound. Raw values for background and maximum [$^{125}$I]-KGF bound were approximately 300 and 12,000 cpm/sample, respectively. Results are representative of three separate experiments.

As an independent approach, the potential peptide/KGF interactions using monoclonal antibodies that neutralize KGF mitogenic activity were analyzed. One such antibody, designated 1G4, was used to develop a radioimmunoassay (RIA) for KGF (see Experimental Procedures). As shown in FIG. 4, immunoprecipitation of [$^{125}$I]-KGF by 1G4 could be competed by unlabeled KGF, but not aFGF, even at a 1000-fold higher concentration. Addition of heparin, which enhances aFGF mitogenic potency, did not cause aFGF to compete in the KGF RIA (FIG. 4). Thus, the binding specificity of 1G4 for KGF was greater than that of the KGFR itself, which binds KGF and aFGF equally well. The results shown in FIG. 4 also indicate that 1G4 has an affinity for KGF comparable to that of the KGFR ($K_d$~200 pM).

In the same assay, peptide 412 (SEQ ID NO 2) displaced [$^{125}$I]-KGF from 1G4 completely, while a control peptide, 341, had no effect (FIG. 4). The concentration of peptide 412 (SEQ ID NO 2) required to achieve 50% displacement was ~1 μM, similar to that required to achieve 50% displacement of [$^{125}$I]-KGF from its receptor (compare FIGS. 2 and 4). Data from both assay systems are consistent with a $K_d$ ~1–2 μM for KGF/peptide 412 (SEQ ID NO 2) interactions. It was also observed that a [$^{125}$I]-KGF/peptide 367 (SEQ ID NO 1) complex could be detected by covalent affinity crosslinking and SDS-PAGE, and that both peptides 367 (SEQ ID NO 1) and 412 (SEQ ID NO 2) specifically displaced [$^{125}$I]-KGF from a crosslinked complex with 1G4 (data not shown). Assuming that 1G4 blocks KGF mitogenic activity by binding to the same site as the receptor, these data indicate that peptide 412 (SEQ ID NO 2) also specifically binds KGF at this site, although with lower affinity.

Figure 5A:
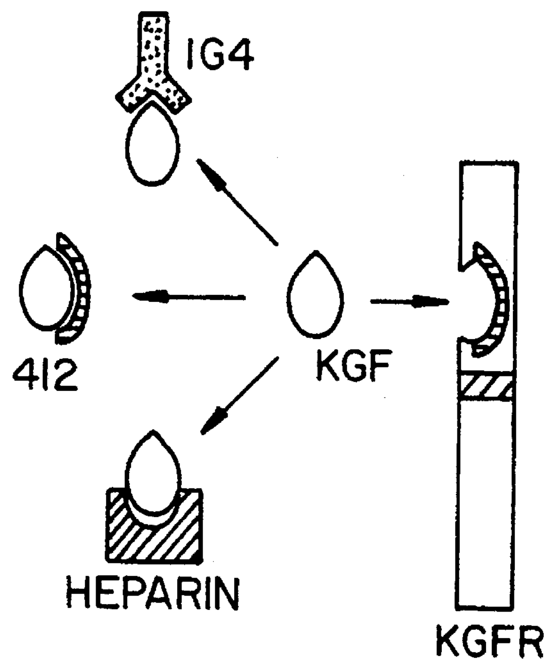
FIG. 5A is a schematic diagram showing antagonists of KGF/receptor interactions include a monoclonal antibody against KGF that neutralizes mitogenic activity (1G4), heparin, and a synthetic peptide corresponding to part of the sequence within the extracellular domain of the KGF receptor encoded by exon K (peptide 412). The schematic shows that each of these antagonists binds to KGF in such a way as to overlap part of the receptor binding site.
Figure 5B:
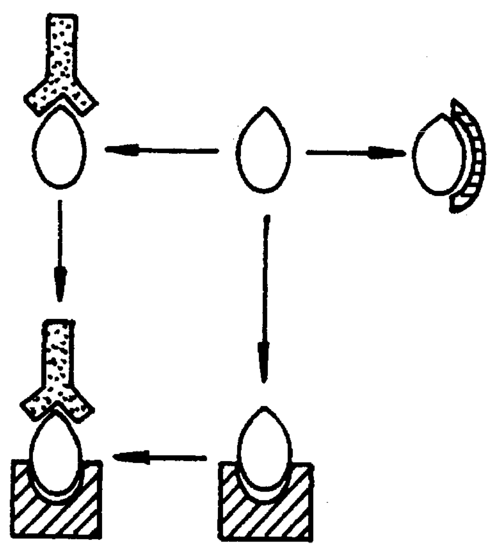
FIG. 5B is a schematic diagram showing that heparin has no effect on the binding of 1G4 to KGF, suggesting that they bind to distinct sites on the growth factor that overlap the receptor binding site.

The above results establish that peptide 412 (SEQ ID NO 2) mimics at least part of the ligand binding site of the KGFR. Whereas heparin enhances AFGF mitogenic activity (Burgess-et al., *Ann. Rev. Biochem.* 58, 575–606 (1989)), it inhibits KGF mitogenesis (Ron et al., supra) and the interaction between KGF and its high affinity receptor. Thus, it was of interest to compare the effects of heparin with those of peptide 412 (SEQ ID NO 2) on 1G4/KGF binding. Heparin, at a concentration 3-fold higher than that required to block 90% of KGF mitogenic activity, had no effect on the interaction between KGF and 1G4 (FIG. 4). Thus 1G4 and heparin, both of which block KGF/KGFR interactions, appear to recognize distinct sites on the KGF molecule. In contrast, the ability of peptide 412 (SEQ ID NO 2) to block 1G4/KGF binding diminished with increasing heparin concentration (FIG. 4). Since heparin does not block KGF/1G4 binding, and peptide 412 (SEQ ID NO 2) does not bind to heparin (data not shown), it is most likely that heparin and peptide 412 (SEQ ID NO 2) compete for the same site on KGF. A model which summarizes these interactions is shown in FIG. 5. Taken together, these data indicate that heparin and 1G4 bind to KGF at separate sites, both of which overlap the peptide 412 (SEQ ID NO 2) binding site.

In conclusion, this example shows that a peptide corresponding to the N-terminal 25 residues encoded by exon K specifically antagonizes KGF and aFGF mitogenicity by interfering with ligand/receptor interaction. Peptide 412 (SEQ ID NO 2) inhibited aFGF mitogenicity mediated by two different FGF receptors, suggesting that it acts by binding directly to the growth factor. This hypothesis was confirmed by the observation that peptide 412 (SEQ ID NO 2) specifically blocked the interaction between KGF and a neutralizing monoclonal KGF antibody. Finally, estimates of the $K_d$ for peptide 412 (SEQ ID NO 2)/KGF interaction predicted from mitogenicity, competitive receptor binding, and radioimmunoprecipitation assay systems were nearly identical. All of these findings lead to the conclusion that peptide 412 (SEQ ID NO 2) binds directly to KGF and aFGF, and thus represents a critical part of the KGFR ligand binding site.

What is claimed is:

1. A composition for inhibiting the binding between keratinocyte growth factor and a keratinocyte growth factor receptor, comprising a KGFR peptide which inhibits binding between keratinocyte growth factor and peptide 367, wherein the KGFR peptide is at least 10 amino acids in length and has a sequence identical to a subsequence of the sequence from position 199 to position 247 of keratinocyte growth factor receptor.

2. The composition of claim 1, wherein the peptide is between about 15 and about 30 residues in length.

3. The composition of claim 1, wherein the peptide is at least 10 amino acids in length and has a sequence identical to the subsequence from position 199 to position 218 of keratinocyte growth factor receptor.

4. A composition comprising a KGFR peptide which inhibits binding between keratinocyte growth factor and a keratinocyte growth factor receptor wherein the peptide is peptide 367 (SEQ ID NO 1).

5. The composition of claim 1, wherein the peptide is at least 10 amino acids in length and has a sequence identical to the subsequence from position 199 to position 223 of keratinocyte growth factor receptor.

6. A composition comprising a KGFR peptide which inhibits binding between keratinocyte growth factor and a keratinocyte growth factor receptor wherein the peptide is peptide 412 (SEQ ID. No. 2).

7. A pharmaceutical composition comprising a pharmaceutically acceptable excipient and a KGFR peptide which inhibits binding between keratinocyte growth factor and peptide 367, wherein the KGFR peptide is at least 10 amino acids in length and has a sequence identical to a subsequence of the sequence from position 199 to position 247 of keratinocyte growth factor receptor.

8. The composition of claim 7, wherein the peptide is between about 15 and about 30 residues in length.

9. The composition of claim 7, wherein the peptide is at least 10 amino acids in length and has a sequence identical to the subsequence from position 199 to position 218 of keratinocyte growth factor receptor.

10. A pharmaceutical composition comprising a pharmaceutically acceptable excipient and a KGFR peptide which inhibits binding between keratinocyte growth factor and a keratinocyte growth factor receptor wherein the peptide is peptide 367 (SEQ ID. No. 1).

11. The composition of claim 7, wherein the peptide is at least 10 amino acids in length and has a sequence identical to the subsequence from position 199 to position 223 of keratinocyte growth factor receptor.

12. A pharmaceutical composition comprising a pharmaceutically acceptable excipient and a KGFR peptide which inhibits binding between keratinocyte growth factor and a keratinocyte growth factor receptor wherein the peptide is peptide 412 (SEQ ID. No. 2).

13. The composition of claim 7, wherein the peptide comprises a D-amino acid or an amino acid mimetic.

14. A composition for inhibiting the binding between keratinocyte growth factor and a keratinocyte growth factor receptor comprising a KGFR peptide which inhibits binding between keratinocyte growth factor and monoclonal antibody 1G4 and wherein said peptide is at least 10 amino acids in length and has a sequence identical to a subsequence of the sequence from position 199 to position 247 of keratinocyte growth factor receptor.

15. A composition comprising a KGFR peptide which inhibits binding between a FGF and a growth factor receptor selected from the group consisting of FGFR-1, FGFR-2 and KGFR and wherein said peptide is at least 10 amino acids in length and has a sequence identical to a subsequence of the sequence from position 199 to position 247 of keratinocyte growth factor receptor.

16. The composition of claim 15, wherein the peptide is peptide 367 (SEQ. ID. NO. 1) or peptide 412 (SEQ. NO. 2).

* * * * *